United States Patent [19]

Langhals et al.

[11] Patent Number: 5,266,700

[45] Date of Patent: Nov. 30, 1993

[54] BIPYRIDYLS AND THEIR USE AS INKS

[75] Inventors: Heinz Langhals, Ottobrunn; Christoph Naumann, Kelkheim-Ruppertshain, both of Fed. Rep. of Germany

[73] Assignee: Riedel-De-Haen, Fed. Rep. of Germany

[21] Appl. No.: 781,261

[22] PCT Filed: Jun. 21, 1990

[86] PCT No.: PCT/EP90/00979

§ 371 Date: Dec. 13, 1991

§ 102(e) Date: Dec. 13, 1991

[87] PCT Pub. No.: WO91/00276

PCT Pub. Date: Jan. 10, 1991

[30] Foreign Application Priority Data

Jun. 27, 1989 [DE] Fed. Rep. of Germany ....... 3921025

[51] Int. Cl.[5] .............. C07D 217/16; C07D 215/20; C07D 213/30
[52] U.S. Cl. .................. 546/140; 546/141; 546/153; 546/257
[58] Field of Search ............. 546/140, 141, 153, 257

[56] References Cited

U.S. PATENT DOCUMENTS 3,751,419  8/1973  Ziegler ........................ 546/140
4,656,278  4/1987  Rossey et al. ................ 546/140

Primary Examiner—Marianne M. Cintins
Assistant Examiner—Michael B. Hydorn
Attorney, Agent, or Firm—Connolly and Hutz

[57] ABSTRACT

Process employing bipyridyls as inks, of the general formula

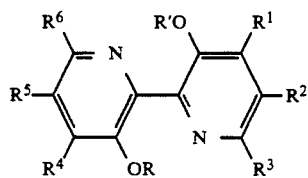

in which

R, R' are, for example, alkyl and $R^1$, $R^2$, $R^3$, $R^4$, $R^5$, $R^6$ are, for example hydrogen or alkyl radicals, or $R^1$ and $R^2$ or $R^2$ and $R^3$, and/or $R^4$ and $R^5$ or $R^5$ and $R^6$ together with the pyridine ring form in isoquinoline or quinoline ring system.

8 Claims, No Drawings

BIPYRIDYLS AND THEIR USE AS INKS

The invention relates to bipyridyls of the general formula I

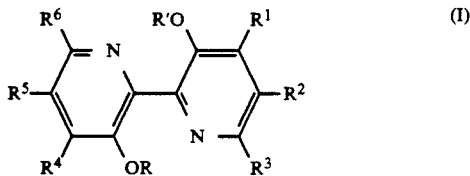

in which

R, R', independently of one another, are hydrogen, alkyl or alkylcarbonyl, $R^1$, $R^2$, $R^3$, $R^4$, $R^5$, $R^6$, independently of one another, are hydrogen, aromatic radicals and/or heterocyclic radicals and/or other non-water-solubilizing radicals and also $R^1$ and $R^2$ or $R^2$ and $R^3$, and/or $R^4$ and $R^5$ or $R^5$ and $R^6$ together with the pyridine ring to which they are bound can be a fused-on phenyl ring, which can also be substituted, under the condition that $R^1$, $R^2$, $R^4$, $R^5$ are not hydrogen if $R^3$ and $R^6$ are hydrogen or methyl, and to processes for their preparation and to their use.

In the bipyridyls of the formula I, one to six, preferably one to four, aromatic radicals and/or heterocyclic radical [sic] and/or other non-water-solubilizing radicals can be present as $R^1$, $R^2$, $R^3$, $R^4$, $R^5$, $R^6$.

$R^1$, $R^2$, $R^3$, $R^4$, $R^5$ and/or $R^6$ as aromatic radicals are in particular mono- to tetracyclic and preferably mono- or bicyclic. Examples of radicals of this type are: phenyl, naphthyl, diphenyl, phenanthryl, fluorenyl, acenaphthyl, pyrenyl, chrysenyl, naphthacenyl.

$R^1$, $R^2$, $R^3$, $R^4$, $R^5$ and/or $R^6$ as heterocyclic aromatic radicals are preferably mono- to tricyclic and can be purely heterocyclic or contain a heterocyclic ring and one or more fused-on benzene rings.

$R^1$, $R^2$, $R^3$, $R^4$, $R^5$ and/or $R^6$ as heterocyclic radicals can be saturated or unsaturated and contain one or more keto, hydroxyl, sulfonyl or sulfone groups. They can contain one or more hetero atoms, in particular from the series comprising O, S and N. Examples of suitable heterocyclic radicals are imides, lactams, sulfoimides.

Examples of heterocyclic aromatic and heterocyclic radicals are: pyridyl, pyrimidinyl, pyrazinyl, triazinyl, furanyl, pyrrolyl, thiophenyl, quinolyl, isoquinolyl, coumarinyl, benzobenzimidazolyl, benzoxazolyl, dibenzofuranyl, benzothiophenyl, dibenzothiophenyl, indolyl, carbazolyl, pyrazolyl, pyrazinyl, imidazolyl, oxazolyl, isooxazolyl, thiazolyl, indazolyl, benzothiazolyl, pyridazinyl, cinnolinyl, quinazolyl, quinoxalyl, phthalazinyl, phthalazinedionyl, phthalimidyl, chromonyl, naphtholactamyl, benzopyridonyl, ortho-sulfobenzimidyl, maleimidyl, naphtharidinyl, benzimidazolonyl, benzoxazolinyl, benzothiazolonyl, benzothiazolinyl, quinazolonyl, quinoxazolinyl, phthalazonyl, dioxapyrimidinyl, pyridonyl, isoquinolonyl, isothiazolyl, benzisoxazolyl, benzisothiazolyl, indazolonyl, acridinyl, acridonyl, quinazolinedionyl, benzoxazinedionyl, benzoxazinonyl and naphthalimidyl.

$R^1$, $R^2$, $R^3$, $R^4$, $R^5$ and/or $R^6$ as aromatic or heterocyclic aromatic or heterocyclic radicals can also contain one or more, in particular one to three, non-water-solubilizing substituents, in particular, for example, those listed below under a to r:

a) Halogen atoms, for example chlorine, bromine, iodine or fluorine.

b) Branched or unbranched alkyl groups preferably having 1 to 18, in particular 1 to 12, in particular 1 to 8, and particularly preferably 1 to 4, C atoms. These alkyl groups can have one or more, preferably one, non-water-solubilizing substituent, such as, for example, fluorine, hydroxyl, cyano, —$OCO^7$, —$OR^8$, —O-$COOR^7$ —$CON(R^8)(R^9)$ or —$OCONHR^7$, in which $R^7$ is alkyl, aryl, such as phenyl or naphthyl, or unsubstituted or halogen-, alkyl- or —O-alkyl-substituted benzyl or a heterocyclic radical, $R^8$ and $R^9$ are hydrogen, unsubstituted or cyano- or hydroxyl-substituted alkyl, $C_3$- to $C_{24}$-cycloalkyl, preferably $C_5$-, $C_6$-, $C_{12}$-, $C_{15}$-, $C_{16}$-, $C_{20}$- and $C_{24}$-cycloalkyl, aryl or heteroaryl, in particular unsubstituted or halogen-, alkyl- or —O-alkyl-substituted phenyl, or in which $R^8$ and $R^9$ together with, in each case, one of the other radicals $R^2$ to $R^4$ form a 5- or 6-membered ring or also a hetero ring, such as, for example, a pyridine, pyrrole, furan or pyran ring. Further possible substituents of the alkyl groups are mono- or dialkylated amino groups, aryl radicals, such as naphthyl or in particular unsubstituted or halogen-, alkyl- or —O-alkyl-substituted phenyl, or furthermore heterocyclic aromatic radicals, such as, for example, 2-thienyl, 2-benzoxazolyl, 2-benzothiazolyl, 2-benzimidazolyl, 6-benzimidazolonyl, 2-, 3- or 4-pyridinyl, 2-, 4- or 6-quinoly or 1-, 3-, 4-, 6- or 8-isoquinolyl radicals.

If the substituents mentioned under b) in turn again contain alkyl, this alkyl can be branched or unbranched and preferably contain 1 to 18, in particular 1 to 12, especially 1 to 8, and particularly preferably 1 to 4, C atoms.

Examples of unsubstituted and substituted alkyl groups representing b) are: methyl, ethyl, n-propyl, isopropyl, n-butyl, sec-butyl, tert-butyl, tert-amyl, n-hexyl, 1,1,3,3-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, trifluoromethyl, trifluoroethyl, cyanomethyl, methoxycarbonylmethyl, acetoxymethyl or benzyl.

c) The group —$OR^{10}$, in which $R^{10}$ is hydrogen, substituted or, preferably, unsubstituted alkyl, aryl, for example naphthyl or in particular unsubstituted phenyl, $C_3$ to $C_{24}$-cycloalkyl, preferably $C_5$-, $C_6$-, $C_{12}$-, $C_{15}$-, $C_{16}$-, $C_{20}$, and $C_{24}$-cycloalkyl, aryl or heteroaryl, in particular unsubstituted or halogen-, alkyl- or —O-alkyl-substituted phenyl where the alkyl group has preferably 1 to 4 C atoms. Alkyl appearing in the definitions of $R^{10}$ can, for example, have one of the number of C atoms mentioned under b) as preferred. Examples of $R^{10}$ are: methyl, ethyl, n-propyl, isopropyl, n-butyl, sec-butyl, tert-butyl, tert-amyl, n-hexyl, 1,1,3,3-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, trifluoromethyl, trifluoroethyl, cyanomethyl, methoxycarbonylmethyl, acetoxymethyl, benzyl, phenyl, o-, m- or p-chlorophenyl, o-, m-, or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl or pyranylmethyl.

e) The cyano groups.

f) The group of the formula —$N(R^8)(R^9)$, in which $R^8$ and $R^9$ have the meaning given under b). Examples are: amino, methylamino, dimethylamino, ethylamino, diethylamino, isopropylamino, 2-hydroxyethylamino, 2-hydroxypropylamino, N,N-bis(2-hydroxyethyl)amino, cyclopentylamino, cyclohexylamino, cyclododecylamino, cyclopentadecylamino, cyclohecadecylamino [sic], cycloeicosanylamino, cyclotetracosanylamino, phenylamino, N-methylphenylamino, benzylamino, dibenzylamino, piperidyl or morpholyl.

g) The group of the formula —COR$^7$, in which R$^7$ has the meaning given under b). Examples of R$^7$ are: methyl, ethyl, n-propyl, isopropyl, n-butyl, sec-butyl, tert-butyl, tert-amyl, n-hexyl, 1,1,3,3-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, trifluoromethyl, trifluoroethyl, cyanomethyl, methoxycarbonylmethyl, acetoxymethyl, benzyl, phenyl, o-, m- or p-chlorophenyl, o-, m-, or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl, pyranylmethyl, benzyl or furfuryl.

h) The group of the formula —N(R$^{11}$)COR$^7$, in which R$^7$ has the meaning given under b), R$^{11}$ is hydrogen, alkyl which is unsubstituted or substituted in particular by OH, cyano, C$_1$ to C$_4$-alkoxy, —O-COR$^5$, for example methyl, ethyl, n-propyl, isopropyl, n-butyl, sec-butyl, n-hexyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, cyanomethyl, methoxycarbonylmethyl, acetoxymethyl, benzyl, phenyl, in particular phenyl which is unsubstituted or substituted by halogen, alkyl, in particular having 1 to 4 C atoms or —O-alkyl, in particular having 1 to 4 C atoms, for example o-, m- or p-chlorophenyl, o-, m-, or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl, pyranylmethyl, benzyl or furfuryl. Any alkyl appearing in the definitions of R$^{11}$ can, for example, have one of the number of C atoms mentioned under b) as preferred. Examples are: acetylamino, propionylamino, butyrylamino, benzoylamino, p-chlorobenzoylamino, p-methylbenzoylamino, N-methylacetamino, N-methylbenzoylamino, N-succinimido, N-phthalimido or N-(4-amino)phthalimido.

i) The group of the formula —N(R$^{10}$)COOR$^7$, in which R$^7$ and R$^{10}$ have the meaning given under b) and c), respectively. Examples are the groups —NHCOOCH$_3$, —NHCOOC$_2$H$_5$ or —NHCOOC$_6$H$_5$.

j) The group of the formula —N(R$^{10}$)CON(R$^8$)(R$^9$), in which R$^8$, R$^9$ and R$^{10}$ have the meaning given under b) and c), respectively. Examples are: ureido, N-methylureido, N-phenylureido or N,N'-2',4'-dimethylphenylureido.

k) The group of the formula —NHSO$_2$R$^7$, in which R$^7$ has the meaning given under b). Examples are: methylsulfonylamino, phenylsulfonylamino, p-tolylsulfonylamino or 2-naphthylsulfonylamino.

l) The groups of the formula —SO$_2$R$^7$ or —SOR$^7$, in which R$^7$ has the meaning given under b). Examples are: methylsulfonyl, ethylsulfonyl, phenylsulfonyl, 2-naphthylsulfonyl, phenylsulfoxidyl [sic].

m) The group of the formula —SO$_2$OR$^7$, in which R$^7$ has the meaning given under b). Examples of R$^7$ are: methyl, ethyl, phenyl, o-, m-, or p-chlorophenyl, o-, m-, or p-methylphenyl, 1- or 2-naphthyl.

n) The group of the formula —CON(R$^8$)(R$^9$), in which R$^8$ and R$^9$ have the meaning given under b). Examples are: carbamoyl, N-methylcarbamoyl, N-ethylcarbamoyl, N-phenylcarbamoyl, N,N-dimethylcarbamoyl, N-methyl-N-phenylcarbamoyl, N-1-naphthylcarbamoyl or N-piperdylcarbamoyl [sic].

o) The group of the formula —SO$_2$N(R$^8$)(R$^9$), in which R$^8$ and R$^9$ have the meaning given under b). Examples are: sulfamoyl, N-methylsulfamoyl, N-ethylsulfamoyl, N-phenylsulfamoyl, N-methyl-Nphenylsulfamoyl or N-morpholylsulfamoyl.

p) The group of the formula —N═N—R$^{12}$, in which R$^{12}$ is the radical of a coupling component or a phenyl radical which is unsubstituted or substituted by halogen, alkyl or —O-alkyl. Any alkyl appearing in the definitions of R$^{12}$ can, for example, have one of the number of C atoms given under b) as preferred. Examples of R$^{12}$ are: the acetoacetarylide, pyrazolyl, pyridonyl, o-, p-hydroxyphenyl, o-hydroxynaphthyl, p-aminophenyl or p-N,N-dimethylaminophenyl radicals.

q) The group of the formula —OCOR$^7$, in which R$^7$ has the meaning given under b). Examples of R$^7$ are: methyl, ethyl, phenyl, o-, m- or p-chlorophenyl.

r) The group of the formula —OCONHR$^7$, in which R$^7$ has the meaning given under a). Examples of R$^7$ are: methyl, ethyl, phenyl, o-, m-, or p-chlorophenyl.

R$^1$, R$^2$, R$^3$, R$^4$, R$^5$ and/or R$^6$ as non-water-solubilizing radicals are in particular those radicals given above under a to r.

R$^1$ and R$^2$ or R$^2$ and R$^3$ and/or R$^4$ and R$^5$ or R$^5$ and R$^6$ together with the pyridine ring to which they are bound can also form a fused-on phenyl ring. These fused-on phenyl rings can also be substituted by 1 to 3, preferably one substituent. Suitable substituents are the aromatic, heteroaromatic and non-water-solubilizing radicals mentioned in the definitions of R$^1$ to R$^6$. R and R' as alkyl radicals have in particular 1 to 4 C atoms. R and R' as alkylcarbonyl radicals have in particular 1 to 4 C atoms in the alkyl radical. Of the radicals R and R', one is preferably hydrogen. Particularly preferably, both R and R' are hydrogen.

Of the compounds according to the invention, those are preferred in which R$^1$, R$^2$, R$^3$, R$^4$, R$^5$, R$^6$, independently of one another, are hydrogen; halogen; alkyl having 1 to 18 C atoms; alkyl having 1 to 18 C atoms and substituted by halogen, hydroxyl, cyano, —OCOR$^7$, —OR$^8$, —OCOOR$^7$, —CON(R$^8$)(R$^9$), —OCONHR$^7$, (C$_1$ to C$_{18}$)alkylamino, di-(C$_1$ to C$_{18}$)alkylamino, naphthyl, phenyl, phenyl substituted by halogen, C$_1$- to C$_{18}$-alkyl or C$_1$- to C$_{18}$-alkoxy, 2-thienyl, 2-, 3- or 4-pyridinyl, 2-benzoxazolyl, 2-benzothiazolyl, 2-benzimidazolyl, 6-benzimidazolyl, 2-, 4- or 6-quinolyl or 1-, 3-, 4-, 6- or 8-isoquinolyl radicals; —OR$^{10}$; —CN; —N(R$^8$)(R$^9$); —COR$^7$; —N(R$^{11}$)COR$^7$; —N(R$^{10}$)COOR$^7$; —N(R$^{10}$)CON(R$^8$)(R$^9$); —NHSO$_2$R$^7$; —SO$_2$R$^7$; —SO$_2$OR$^7$; —CON(R$^8$)(R$^9$); —SO$_2$(R$^8$)(R$^9$); —N═N—R$^{12}$; —OCOR$^7$; —OCONHR$^7$; or phenyl, naphthyl, biphenyl, phenanthryl, fluorenyl, acenaphthyl, pyrenyl, chrysenyl, naphthacenyl, pyridyl, plyrimidinyl, pyrazinyl, triazinyl, furanyl, pyrrolyl, thiophenyl, quinolyl, isoquinolyl, coumarinyl, benzofuranyl, benzimidazolyl, benzoxazolyl, dibenzofuranyl, benzothiophenyl, dibenzothiophenyl, indolyl, carbazolyl, pyrazolyl, pyrazinyl, imidazolyl, oxazolyl, isooxazolyl, thiazolyl, indazolyl, benzothiazolyl, pyridazinyl, cinnolinyl, quinazolyl, quinoxalyl, phthalazinyl, phthalazinedionyl, phthalimidyl, chromonyl, naphtholactamyl, benzopyridonyl, ortho-sulfobenzimidyl, maleimidyl, naphtharidinyl, benzimidazolonyl, benzoxazolinyl, benzothiazolonyl, benzothiazolinyl, quinazolonyl, quinoxazolinyl, phthalazonyl, dioxapyrimidinyl, pyridonyl, isoquinolonyl, isothiazolyl, benzisoxazolyl, benzisothiazolyl, indazolonyl, acridinyl, acridonyl, quinazolinedionyl, benzoxazinedionyl, benzoxazinonyl and naphthalimidyl, which can also be substituted by one or more, preferably one or two, of the following substituents: halogen, alkyl having 1 to 18 C atoms, $-OR^{10}$, $-CN$, $-N(R^8)(R^9)$, $-COR^7$, $-N(R^{11})COR^7$, $-N(R^{10})COOR^7$; $-N(R^{10})CON(R^8)(R^9)$; $-NHSO_2R^7$; $-SO_2R^7$; $-SO_2OR^7$, $-CON(R^8)(R^9)$, $-SO_2(R^8)(R^9)$; $-N=N-R^{12}$, $-OCOR^7$, $-OCONHR^7$, alkyl having 1 to 18 C atoms substituted by halogen, hydroxyl, cyano, $-OCOR^7$, $-OR^8$, $-OCOOR^7$, $-CON(R^8)(R^9)$, $-OCONHR^7$, ($C_1$ to $C_{18}$) alkylamino, di-($C_1$ to $C_8$)alkylamino, naphthyl, phenyl, phenyl substituted by halogen, $C_1$- to $C_{18}$-alkyl or $C_1$- to $C_{18}$-alkoxy, 2-thienyl, 2-, 3- or 4-pyridinyl, 2-benzoxazolyl, 2-benzothiazolyl, 2-benzimidazolyl, 6-benzimidazolyl, 2-, 4- or 6-quinolyl or 1-, 3-, 4-, 6- or 8-isoquinolyl radicals;

$R^7$ is alkyl having 1 to 18 C atoms; $C_1$- to $C_{18}$-alkyl which is substituted by halogen, hydroxyl, cyano, $-OR^8$, $-CON(R^8)(R^9)$, ($C_1$ to $C_{18}$)alkylamino, di-($C_1$ to $C_{18}$)alkylamino, phenyl, 2-thienyl, 2-benzoxazolyl, 2-benzothiazolyl, 6-benzimidazolyl, 2-, 3- or 4-pyridinyl, 2-, 4- or 6-quinolyl or 1-, 3-, 4-, 6- or 8-isoquinolyl or by phenyl substituted by halogen, $C_1$- to $C_{18}$-alkyl, $C_1$- to $C_{18}$-alkoxy;

$R^8$ is hydrogen, $C_1$- to $C_{18}$-alkyl, $C_1$- to $C_{18}$-alkyl which is substituted by cyano or hydroxyl $C_3$ to $C_{24}$-cycloalkyl, phenyl, phenyl substituted by halogen, $C_1$- to $C_{18}$-alkyl, $C_1$- to $C_{18}$-alkoxy;

$R^9$ is hydrogen, $C_1$- to $C_{18}$-alkyl, $C_1$- to $C_{18}$-alkyl which is substituted by cyano or hydroxyl, phenyl, phenyl substituted by halogen, $C_1$- to $C_{18}$-alkyl, $C_1$- to $C_{18}$-alkoxy;

$R^{10}$ is hydrogen, $C_1$ to $C_{18}$ alkyl, phenyl, $C_3$ to $C_{24}$ cycloalkyl, $R^{11}$ is hydrogen, unsubstituted or hydroxyl-, cyano-, $C_1$ to $C_4$-alkoxy- or $-OCOR^7$-substituted $C_1$ to $C_{18}$ alkyl; $R^{12}$ is the radical of a coupling component or a phenyl radical which is unsubstituted or substituted by halogen, $C_1$- to $C_{18}$-alkyl, $C_1$- to $C_{18}$-alkoxy and in which $R^8$ and $R^9$ together with one of the other radicals can also form a 5- or 6-membered ring or hetero ring and in which also $R^1$ and $R^2$ or $R^2$ and $R^3$ and/or $R^4$ and $R^5$ or $R^5$ and $R^6$ together with the pyridine ring to which they are bound can be a fused-on phenyl ring, which can be unsubstituted or substituted by one, two or three substituents, preferably one or two substituents from the series comprising hydrogen; halogen; alkyl having 1 to 18 C atoms; alkyl having 1 to 18 C atoms substituted by halogen, hydroxyl cyano, $-OCOR^7$, $-OR^8$, $-OCOOR^7$, $-CON(R^8)(R^9)$, $-OCONHR^7$, (C to $C_{18}$)alkylamino, di-($C_1$ to $C_{18}$)alkylamino, naphthyl, phenyl, phenyl substituted by halogen, $C_1$- to $C_{18}$-alkyl or $C_1$- to $C_{18}$-alkoxy, 2-thienyl, 2-, 3- or 4-pyridinyl, 2-benzoxazolyl, 2-benzothiazolyl, 2-benzimidazolyl, 6-benzimidazolyl, 2-, 4- or 6-quinolyl or 1-, 3-, 4-, 6- or 8-isoquinolyl radicals; $-OR^{10}$; $-CN$; $-N(R^8)(R^9)$; $-COR^7$; $-N(R^{11})COR^7$; $-N(R^{10})COOR^7$; $-N(R^8)CON(R^8)(R^9)$; $-NHSO_2R^7$; $-SO_2R^7$; $-SO_2OR^7$, $-CON(R^8)(R^9)$; $-SO_2(R^8)(R^9)$; $-N=N-R^{12}$; $-OCOR^7$; $-OCONHR^7$.

Preference is also given to those compounds according to the invention in which both R and $R^2$ and $R^4$ and $R^5$ together with the pyridine ring to which they are bound each form a fused-on phenyl ring, which may also be substituted.

Furthermore, preference is given to those compounds according the invention in which both R and $R^2$ and $R^4$ and $R^5$ together with the pyridine ring to which they are bound each form a fused-on phenyl ring, which may also be substituted.

Particular preference is given to the following compounds of the formulae II to V:

4,4'-bishydroxy-3,3'-biisoquinoline of the formula II:

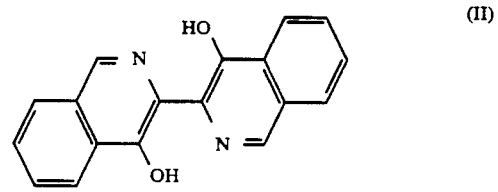

3,3'-bishydroxy-2,2'-biquinoline of the formula III

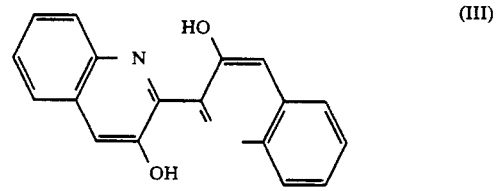

3-methoxy-3'-hydroxy-2,2'-biquinoline of the formula IV:

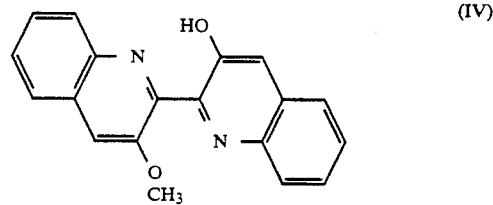

3,3'-bismethoxy-2,2'-biquinoline of the formula V:

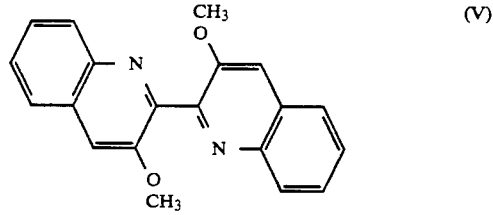

The compounds according to the invention cannot be prepared by the Zincke rearrangement. Reductive organometallic coupling of suitably substituted or homologous 2-bromo-3-hydroxypyridines it not feasible for preparing the compounds according to the invention where R or R' is hydrogen, since the acidity of the OH groups is prohibitive for most organometallic reactions.

Surprisingly, it has now been found that even the compounds according to the invention having acidic OH groups can be prepared by aryl coupling in the presence of zinc. Accordingly, the invention also relates to a process for the preparation of bipyridyls of the general formula Ia

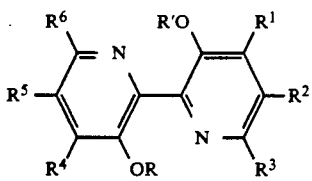

in which

R, R', independently of one another, are hydrogen, alkyl or alkylcarbonyl, $R^1$, $R^2$, $R^3$, $R^4$, $R^5$, $R^6$, independently of one another, are aromatic radicals, heterocyclic radicals or other non-water-solubilizing radicals and $R^1$ and $R^2$ or $R^2$ and $R^3$ and/or $R^4$ and $R^5$ or $R^5$ and $R^6$ together with the pyridine ring to which they are bound are a fused-on phenyl ring, which may also be substituted, characterized in that a compound of the general formula VI

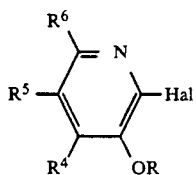

in which R, $R^4$, $R^5$, $R^6$ have the abovementioned meanings and Hal is a halogen atom, are brought into contact with zinc and the alkyl or alkylcarbonyl radicals R and/or R' are, if desired, eliminated in a manner known per se from the compound formed by the coupling reaction of the general formula Ia and replaced by hydrogen.

Hal is, for example, a fluorine, chlorine, bromine or iodine atom. Preferably, Hal is a bromine atom. The zinc is used in elemental form, for example in the form of rods, granules or dust. The use of zinc dust is preferred. The reaction is carried out in a solvent, preferably in dimethylformamide (DMF). The zinc is advantageously used in pure form.

The reaction is preferably carried out at temperatures of between −20° and 150° C., particularly preferably at temperatures of 0° to 100° C. and very particularly preferably at temperatures of between 20° and 60° C.

The yields can be increased by carrying out the reaction in the presence of $Ni^{(o)}$ and of one or more phosphorus compounds which complex the $Ni^{(o)}$, such as, for example, triphenyl phosphine. The nickel can be used in elemental form, preferably as a powder. However, it is advantageously produced in situ from a nickel compound. The nickel compounds which can be used are nickel(III) compounds, for example nickel(III) salts, preferably nickel(II) compounds, in particular nickel-(II) salts. Examples of suitable nickel salts are nickel(II) chloride, which may also be used in the form of a hydrate, for example as $NiCl_2 \times 6H_2O$.

The use of $Ni^{(o)}$ in the presence of a phosphorus compound which complexes the $Ni^{(o)}$ removes the reaction product of the formula I continuously from the reaction mixture and brings it into a form which can be easily precipitated. This simplifies the synthesis method and moreover activates the surface of the zinc. The Ni complex of the reaction product can then be precipitated after the reaction. This very significantly simplifies the workup.

Workup is preferably carried out by using sodium hydroxide solution or potassium hydroxide solution, preferably sodium hydroxide solution, or preferably by using ammonia. The use of metal-complexing agents during the workup, such as, for example, cyanides, in particular of potassium cyanide or sodium cyanide, of which sodium cyanide is preferred, is also favorable. Synthesis and workup are advantageously monitored via the fluorescence of the compounds. For preparing the substances in high purity, a chromatographic purification process or extractive recrystallization by the method of H. Langhals, Chem. Ber. 118 (1988), 4[illegible] can be used.

The process according to the invention is also suitable for preparing compounds of the formula I in which the radicals $R^1$, $R^2$, $R^4$ and $R^5$ can also be hydrogen if $R^3$ and $R^6$ are hydrogen or methyl. These compounds are designated by the formula Ia.

In some cases, the process according to the invention produces extremely sparingly soluble compounds, as in the case of 3,3'-dihydroxy-2,2'-biquinoline, which can be separated off from the zinc hydroxide formed in the reaction only with difficulty. In these cases, it is more favorable to use a compound of the formula VI in which R is alkyl having in particular 1 to 4 C atoms, preferably methyl, or alkylcarbonyl having in particular 1 to 4 C atoms in the alkyl radical, and to eliminate the protective groups in a manner known per se in succession or simultaneously from the dimerization product of the formula I obtained in the coupling reaction. When 3,3'-dihydroxy-2,2'-biquinoline is prepared, it is, for example, more favorable to prepare the more soluble 3,3'-dimethoxy-2,2'-biquinoline by coupling and to convert the methoxy groups subsequently to OH groups by ether cleavage. When hydrobromic acid is used, this leads to the formation of the 3-methoxy-3'-hydroxy-2,2'-biquinoline of the formula IV, which has also interesting fluorescence properties. If in contrast hydroiodic acid is used, the desired 3,3'-dihydroxy-2,2'-biquinoline of the formula V is obtained as a colorless substance.

The reaction can also be carried out in the presence of small amounts of water. Accordingly, the solvents used need not be dried. It is also possible to use hydrated NI(II) salts. The use of an inert gas, such as nitrogen or argon, increases the yield but is not essential for the reaction.

Using the process according to the invention, the compounds of the formula VI in which Hal, $R^4$, $R^5$ and $R^6$ have the meaning already mentioned and R is hydrogen, alkyl or alkylcarbonyl are converted by coupling into symmetrical dimerization products of the formula I or Ia, i.e. the meanings of $R^6$ and $R^1$, of $R^5$ and $R^2$, of $R^4$ and $R^1$, and of R and R' are mutually identical.

The compounds required as starting materials of the general formula VI, in which $R^4$, $R^5$, $R^6$ and Hal have the meanings already mentioned and R is hydrogen alkyl or alkylcarbonyl, are known or can be easily prepared in a manner known per se.

The synthesis process according to the invention described makes it possible to synthesize symmetrical bipyridyls in high yields. Unsymmetrical bipyridyls of the formula I and Ia, i.e. those in which $R^1$ and $R^4$, $R^2$ and $R^5$, $R^3$ and $R^6$ each have at least one different meaning, can be prepared by coupling a compound of the general formula VI, to give an organotin compound, for example using trimethyltin chloride to give the compound VII

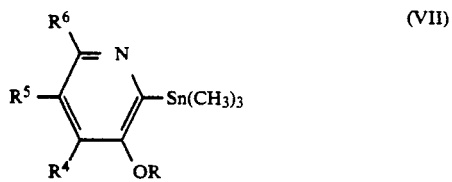

and then coupling this compound, using Ni(o) or Pd(o) compounds in the presence of a phosphine compound in particular of thriphenylphosphine [sic] with a compound VIII

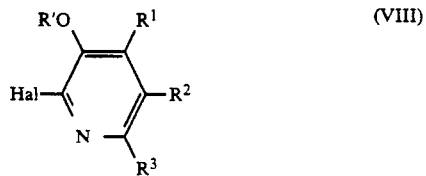

in which $R^1$, $R^2$, $R^3$, $R'$ and Hal have the meanings already mentioned.

The bipyridyls of the general formula I and the bipyridyls of the formula Ia preparable by the process according to the invention have a long-wave solid-state fluorescence. In the solid state, they also show short-wave absorption (in the UV region) and long-wave fluorescence (red). Owing to the large Stokes shift, they are particularly suitable in particular for applications in safety markings.

The compounds according to the invention of the formula I and the compounds of the formula Ia preparable by the process according to the invention can be used for various purposes. In these applications, the fluorescence and the large Stokes shift play a particular role. Accordingly, they can be used, for example, in in [sic] dye lasers and scintillation counters and in fluorescent solar collectors. A particular advantage here is that, owing to the large Stokes shift, no light losses due to reabsorption of the fluorescence light occur even in the case of long light paths (negligibly small spectral overlap).

Furthermore, the solid-state fluorescence of the substances is of importance, since it makes them particularly suitable for marking purposes, in particular for safety markings. The 4,4'-dihydroxy-3,3'-biisoquinoline has particularly interesting properties. It is a light orange substance which has an intensive red solid-state fluorescence and thus a very large Stokes shift even as a solid. In this substance, the ESIPT Förster mechanism of proton transfer probably proceeds with high efficiency especially in the solid state. This property makes the substance particularly interesting for marking purposes, since upon exposure to normal daylight which, as is known, has a low proportion of UV light, no appreciable fluorescence takes place, which means that the marking is invisible, since the substance in addition has only a weak color of its own. By using UV light (for example the light from a mercury vapor lamp) the conspicuous red fluorescence of the substance shows up. The large Stokes shift is not only of interest for the visual detection of the marking but also for detection by machine, since any scattered excitation light can thereby easily be cut out by means of an optical filter, so that only the fluorescence light impinges on the detector used. Possible applications of the substance are not only the marking of products in order to be detected by machine (for example for sorting processes), but also the recycling of organic materials. An invisible and thus non-interfering marking can be applied on the material by means of the substance mentioned, thus making it possible later on to separate out the material by machine. Normally, such large Stokes shifts in solid-state fluorescence—colorless or lightly colored substances having a red solid-state fluorescence—could only be achieved with chelates of rare earths, for example $EU^{3+}$. This, however, has various disadvantages, such as, for example, an increased I.S.C. rate coupled with the potential formation of singlet oxygen, formation of triplet states in the substrates used by energy transfer of the consumed dyes caused, inter alia, by impurities (for example Th from the monazite sand as the inorganic starting materials for the rare earths). These problems no longer exist in the dyes according to the invention of the formula I and the dyes preparable by the process according to the invention of the formula Ia on purely organic bases, which contain only carbon, hydrogen, oxygen and nitrogen.

Some of the substances according to the invention of the formula I and the compounds preparable by the process according to the invention of the formula Ia have the characteristic property of showing intensive fluorescence from the $S_2$ state. Usually, $S_2$ fluorescences are very weak, but in the case of the compounds mentioned here the quantum yields reach 30%. This is related to the specific electronic and structural conditions of the substances. The $S_2$ fluorescence is of interest for applications of the compounds, since a dual fluorescence occurs in combination with the $S_1$ fluorescence. This makes it possible, for example, to tune a dye laser over a fairly wide range.

Furthermore, the compounds according to the invention of the formula I and the compounds preparable by the process according to the invention of the formula Ia can be used as chelating agents. In some cases, this changes the fluorescence quite substantially. The chelate formation with metals can induce it or erase it in other compounds or shift it to a different wavelength region, since the intramolecular ESIPT Förster process of proton transfer can now no longer take place. This makes it possible to use the dyes, on the one hand, as fluorescence indicators and, on the other, also directly for fluorometric determination of heavy metals. This is of importance where high sensitivity is required or where the solution to be tested is cloudy or colored—especially in the case of cloudy solutions a photometric determination (which is based on absorption) is full of errors.

Since many of the compounds according to the invention of the formula I and the compounds preparable by the process according to the invention of the formula Ia can be sublimed at higher temperatures without decomposition, they can also be applied selectively to a substrate by means of sublimation processes. This is of interest, on the one hand, for sublimation printing processes and, on the other, also for printers in electronic data processing in which it is desired to produce a fluorescent print or marking.

The compounds according to the invention of the formula I and the compounds preparable by the process according to the invention of the formula Ia can thus be used in a manner known per se, for example, in dye lasers, in highly sensitive detection processes based on the fluorescence (see C. Aubert, J. Fünfschilling, I. Zschokke-Gränacher and H. Langhals, Z. Anlalyt. Chem- 320 (1985) 361), as tracers in biochemical, medical, geological, industrial and scientific applications, in particular for the detection of amino acids in protein studies, it being possible to achieve increased accuracy via the ESIPT mechanism; in scintillators; in optical light-collecting systems; in fluorescent solar collectors; in fluorescence-activated displays; in cold light sources for light-induced polymerization in order to prepare plastics; for material testing, for example in the production of semiconductor circuits; for the study of microstructures of integrated semiconductor structural components; as photoconductors; in dry-copying systems, laser printers and other recording systems (xerox process); in photographic processes; in display, illumination or image converter systems, in which excitation takes place via electrons, ions or UV radiation, for example in fluorescent displays, Braun tubes or fluorescent tubes; as part of an integrated semiconductor circuit, either as dye or in combination with other semiconductors, for example in the form of an epitaxy; in chemiluminescent systems, for example in chemiluminescent lamps, in luminescent immune essays [sic] or other luminescent detection procedures; as signaling inks, preferably for the optical highlighting of written characters and drawings or other graphic products, for the marking of signs and other articles, in which it is desired to obtain a particular optical color impression; for safety markings, preferably for checks, check cards, bills, coupons, identification papers and the like, in which it is desired to achieve a particular, unmistakable color impression; as additive to other paints, in which it is desired to achieve a specific shade, preference being given in particular to luminescent paints; for the marking of articles for the machine detection of these articles via the fluorescence, preference being given to machine detection of articles for sorting, for example for the recycling of plastics, as fluorescent dyes for machine-readable markings, preference being given to alphanumeric prints or barcodes; for the frequency conversion of light, for example in order to convert short-wave light into longer-wave, visible light; in passive display elements for a wide range of display, notice and marking purposes, for example passive display elements, notice and road signs, such as traffic lights; in ink-jet printers, preferably in homogeneous solution as fluorescent ink; as starting material for superconducting organic materials.

The compounds according to the invention of the formula I and the compounds preparable by the process according to the invention of the formula Ia are furthermore also suitable for the covalent incorporation in polymers and copolymers and as $\beta$-blockers.

The use of the dyes according to the invention of the formula I and the dyes preparable by the process according to the invention of the formula Ia for signaling inks and marking purposes, in particular for safety markings for checks, check cards, credit cards, shares, coupons, construction nodes [sic], identification papers, and the like is preferred.

EXAMPLE 1

3,3'-Dihydroxybipyridyl a) 4.06 g (17.2 mmol) of $NiCl_2 \times 6H_2O$ are dissolved in 75 ml of technical grade DMF (green color). A continuous argon gas stream is passed through the reaction solution. After dissolution of all the $NiCl_2 \times 6H_2O$, 17.92 g (68.96 mmol) of triphenyphosphine [sic] are added. This leads to a dark blue color of the reaction solution due to the complexation with nickel. This solution is heated to 50° C., and, after reaching this temperature, 3.10 g (47.7 mmol) of zinc powder are added. This changes the color of the reaction solution from dark blue via turquoise to red-brown. The red-brown color is characteristic of the formation of an Ni(O) complex. This solution is stirred at 50° C. under argon as the inert gas for a total of 1 hour. 3.00 g (17.2 mmol) of 2-bom-3-hydroxypyridine [sic] are then added to this solution in solid form. After a reaction time of 30 minutes, a red-brown precipitate is formed. The further course of the reaction is monitored by thin-layer chromatography (silica gel/petroleum ether (low-boiling):ether=75:25). After as little as 45 minutes, hardly any educt is left. The reaction is stopped after 2 hours by pouring the still warm reaction solution into 300 ml of 2N sodium hydroxide solution, during which triphenylphosphine is precipitated. The suspension obtained is vigorously stirred for 10 minutes and the product is then filtered off. The solid obtained is suspended once more in 300 ml of 2N NaOH and filtered off again, giving a clear yellow solution. This solution is brought to a pH of 7-6 with concentrated hydrochloric acid, resulting in a light yellow flocculent precipitate of the crude product. In order to obtain as quantitative a precipitation of the crude product as possible, it is recommended to irradiate the solution with a UV lamp, ($\lambda_{max}$=365/366 nm). In this manner, quantitative precipitation can be detected accurately by the change in fluorescence from blue to light green. Care should be taken that the precipitated product has a green solid state fluorescence. Immediately after precipitation, the precipitate obtained is filtered off, washed with water until neutral and dried in vacuo. The crude product obtained is recrystallized from 50 ml of toluene and finally concentrated to 25 ml for crystallization, giving light yellow needles of the pure product.

Yield 0.89 g (55.0%)—melting point: 194°-195° C., mixed melting point 194° C.-$R_F$ (silica gel/petroleum ether (low-boiling): ether=9:1)=0.20.—IR (KBr):$\nu$=3435 cm$^{-1}$, 2541 (m, OH), 1601 (w), 1572 (m, aromatic), 1494 (s), 1442 (s), 1357 (w), 1344 (w), 1307 (s, C—O), 1235 (w), 1116 (m), 1067 (w), 879 (m), 840 (w), 799 (s), 728 (m), 650 (m), 535 (w), 458 (w).

Further processes for the preparation of 3,3'-dihydroxy-2,2'-bipyridyl b) Using ammonia and sodium cyanide for workup. 4.06 g (17.2 mmol) of $NiCl_2 \times 6H_2O$ are dissolved in 75 ml of technical grade DMF (green). A continuous argon gas stream is passed through the reaction solution. After dissolution of all the $NiCl_2 \times 6H_2O$, 17.92 g (68.96 mmol) of triphenylphosphine are added. This leads to a dark blue color of the reaction solution due to the complexation with nickel. This solution is heated to 50° C., and, after reaching this temperature, 3.10 g (47.7 mmol) of zinc powder are added. This changes the color of the reaction solution from dark blue via turquoise to red-brown. The red-brown color is characteristic of the formation of an Ni(O) complex. This solution is stirred at 50° C. under argon as the inert gas for a total of 1 hour. 3.00 g (17.2 mmol) of 2-bromo-3-hydroxypyridine are then added to this solution in solid form. After a reaction time of 30 minutes, a red-brown precipitate is formed. The further course of the reaction is monitored by thin-layer chromatography (silica gel/petroleum ether (low-boiling):ether=75:25). After as little as 45 minutes, hardly any educt is left. The reaction is stopped after 2 hours. The reaction mixture is poured into 400 ml of 28% ammonia:water=1:1. This leaves the red-brown precipitate formed in the reaction undissolved. This phase is extracted with 500 ml of chloroform, which immediately dissolves the brown precipitate. The chloroform phase is brown, while the aqueous phase is green. 8.0 g of sodium cyanide are added to the resulting ammoniacal aqueous phase in order to destroy the complex formed. Upon addition of sodium cyanide, the aqueous phase turns yellow. This solution is brought to a pH of 8 with concentrated hydrochloric acid, resulting in the formation of a brown-beige precipitate having a green solid-state fluorescence. This precipitate is extracted with 400 ml of chloroform and added to the first chloroform phase. The two chloroform phases are concentrated and separated via a column (silica gel/petroleum ether (low-boiling):ether=90:10). The first charge obtained is triphenylphosphine and the next charge gives 0.3 g of contaminated crude product (light brown). This product can be further purified by chromatography. The triphenylphosphine cannot be separated off by sublimation.

Yield 0.30 g (crude product)—melting point 120° C.—$R_F$ (silica gel/petroleum ether (low-boiling):ether)=0.20 (P(Ph)$_3$=0.68). —IR (KBr):$\nu$=3438 cm$^{-1}$, 1572 (m), 1494 (s), 1476 (m), 1442 (s), 1436 (s), 1345 (w), 1307 (s), 1235 (w), 1118 (m), 879 (w), 800 (s), 748 (m), 742 (m), 697 (m), 650 (m), 645 (m).

c) Preparation using sodium cyanide and ammonia after the filtration.

4.06 g (17.2 mmol) of NiCl$_2$×6H$_2$O are completely dissolved in 75 ml of technical grade DMF under a continuous argon gas stream (green color) 17.92 g (68.96 mmol) of triphenylphosphine are then added. This leads to a dark blue color of the reaction solution due to the complexation with nickel. This solution is heated to 50° C., and, after reaching this temperature, 3.10 g (47.7 mmol) of zinc powder are added. This changes the color of the reaction solution from dark blue via turquoise to red-brown. The red-brown color is characteristic of the formation of an Ni(O) complex. This solution is stirred at 50° C. under argon as the inert gas for a total of 1 hour. 3.00 g (17.2 mmol) of 2-bromo-3-hydroxypyridine are added to this solution in solid form. After a reaction time of 30 minutes, a red-brown precipitate is formed. The further course of the reaction is monitored by thin-layer chromatography (silica gel/petroleum ether (low-boiling):ether=9:1). After as little as 45 minutes, hardly any educt is left. The reaction is stopped after 2 hours. The reaction solution is poured into 200 ml of water, resulting in the formation of a voluminous precipitate. 8.0 g of sodium cyanide are then added to the aqueous phase, and the entire mixture is stirred for 10 minutes. This solution is then filtered, resulting in a yellow clear solution. A colorless precipitate remains in the filter, which is suspended in 100 ml of concentrated ammonia and added to the yellow aqueous phase by filtration. The ammoniacal aqueous phase thus obtained is brought to a pH of 8 with concentrated hydrochloric acid, giving a voluminous, yellow solid (green solid-state fluorescence), which is dried over sodium sulfate and concentrated on a rotary evaporator. During evaporation, long yellow slightly sticky needles are obtained (yield of the crude product 0.5 g, melting point 135°-175°). The crude product obtained is recrystallized from 30 ml of toluene, giving the desired product in the form of long, yellow needles.

Yield 0.15 g (9.26%)—melting point 194°-195° C. mixed melting point 195° C.—$R_F$ (silica gel/petroleum ether (low-boiling): ether=9:1)=0.20.—IR (KBr) 3439 cm$^{-1}$, 2632 (m), 536 (m, OH), 1601 (w), 1571 (m, aromatic, 1492 (s), 1441 (s), 1357 (w), 1345 (w), 1306 (s, C—O), 1253 (w), 1235 (w), 1116 (m), 1067 (w), 879 (m), 840 (w), 799 (s), 728 (m), 650 (m), 645 (m), 535 (w).

EXAMPLE 2

3,3'-Dimethoxy-2,2'-bipyridyl a) 2-Bromo-3-methoxypyridine 5.93 g (90.0 mmol) of 85% powdered potassum [sic] hydroxide are suspended in 30 ml of DMSO and heated to 50° C. under argon as the inert gas. 2.54 g (14.6 mmol) of 2-bromo-3-hydroxypyridine dissolved in 10 ml of DMSO are added dropwise to this suspension. This solution is stirred for another 10 minutes, after which 12.3 g (5.30 ml, 33.1 mmol) of methyl iodide are added dropwise over a period of 2 minutes. The addition takes place at such a rate that the reaction temperature is always between 50°-55° C. The reaction [sic] is then stirred at this temperature for another 10 minutes. The finished reaction solution is finally poured onto 100 ml of ground ice. The crude product obtained is recrystallized from ether/petroleum ether (4:1).

Yield 2.00 g (70%)—melting point 44.0° C.

b) 3,3'-Dimethoxy-2,2'-bipyridyl 6.24 g (26.5 mmol) of NiCl$_2$×6H$_2$O are dissolved in 125 ml of technical grade DMF (green color). A continuous argon gas stream is passed through the reaction solution. After dissolution of all the NiCl$_2$×6H$_2$O, 27.5 g (106 mmol) of triphenylphosphine are added. This leads to a dark blue color of the reaction solution due to the complexation with nickel. This solution is heated to 50° C., and, after reaching this temperature, 4.50 g (69.2 mmol) of zinc powder are added. This changes the color of the reaction solution from dark blue via turquoise to red-brown. The red-brown color is characteristic of the formation of an Ni(O) complex. This solution is stirred at 50° C. under argon as the inert gas for a total of 1 hour. 5.00 g (26.5 mmol) of 2-bromo-3-methoxypyridine are then added to this solution in solid form. After a reaction time of 30 minutes, a red-brown precipitate is formed. The further course of the reaction is monitored by thin-layer chromatography (silica gel/petroleum ether (low-boiling):ether=75:25). The reaction is stopped after 1.5 hours. The still warm reaction solution is poured into 500 ml of half-concentrated ammonia, during which triphenylphosphine precipitates. The suspension obtained is vigorously stirred for 10 minutes and then extracted with a total of 300 ml of methylene chloride. The methylene chloride phase is extracted with a total of 250 ml of 4N hydrochloric acid. This gives a clear yellow aqueous solution, which is brought to a pH of 7 with 10% strength sodium hydroxide solution. This leads to the formation of a light yellow flocculent precipitate of the crude product, which is recrystallized from 50 ml of toluene and finally concentrated to 25 ml for crystallization. Colorless crystals of the pure product are obtained.

Yield 1.59 g (55.5%)—melting point 136° C.—mixed melting point 137° C.—$R_F$ (silica gel/chloroform:methanol 9:1)=0.71.—IR (KBr):$\nu$=3436 cm$^{-1}$, 3070 (w, aromatic), 3030 (w, aromatic), 2970 (m, aliphatic), 2950 (m, aliphatic), 2840 (m, aliphatic), 1589 (m, aromatic), 1579 (m, aromatic), 1565 (m, aromatic), 1470 (s), 1456 (s), 1420 (s), 1272 (s, C—O—C), 1200 (s, C—O—C), 1180 (s, C—O—C), 1131 (s, C—O—C), 1119 (s), 1079 (s), 1069 (w), 1007 (s), 801 (s), 782 (m), 767 (m), 621 (s), 568 (m). —UV/VIS (chloroform):$\lambda_{max}$ ($\epsilon$)=288 nm (10180).—$^1$H-NMR (CDCl$_3$/TMS): $\delta$=3.75 (s, 6H, OCH$_3$), 7.27 (mc, 4H, 4-H, 4'-H, 5-H, 5'-H), 8.27 (m, 2H, 6-H, 6'-H).

EXAMPLE 3

3,3'-Dihydroxy-6,6'-dimethyl-2,2'-bipyridyl a) 2-Bromo-3-hydroxy-6-methylpyridine 16.0 g (0.14 mol) of 3-hydroxy-6-methylpyridine are dissolved in 122 ml of 30% strength HBr in glacial acetic acid, and the solution is heated to 70° C. 70.4 [lacuna] (24.3 ml, 0.47 mol) of bromine are added dropwise at this temperature over a period of 1 hour. The reaction solution is stirred at this temperature for another 5 hours. After the reaction is complete, nitrogen is passed through the reaction solution for 2 hours (to drive off bromine). The reaction solution is then concentrated to 50 ml in vacuo. In this manner, an orange-red paste of the hydrobromide of the desired compound is obtained. The hydrobromide is boiled in 400 ml of water and then brought to a PH of 8 with a 1N bicarbonate solution. The dirty brown crude product obtained is recrystallized from water/methanol (2:3), giving colorless crystals of the pure product.

Yield 14.2 g (54.1%)—melting point 193°–194° C. (ref[12]) 191°192° C.).—$^1$H-NMR ((D$_6$)DMSO/TMS): 2.33 (s, 3H, CH$_3$), 7.03 (d, J$_{4,5}$=8.0 Hz 1H, 4-H), 7.18 (d, J$_{5,4}$=8.0 Hz, 1H, 5-H).

b) 3,3'-Dihydroxy-6,6'-dimethyl-2,2'-bipyridyl 4.06 g (17.2 mmol) of NiCl$_2$×6H$_2$O are dissolved in 75 ml of technical grade DMF (green color). A continuous argon gas stream is passed through the reaction solution. After dissolution of all the NiCl$_2$×6H$_2$O, 17.92 g (68.96 mmol) of triphenyphosphine [sic] are added. This leads to a dark blue color of the reaction solution due to the complexation with nickel. This solution is heated to 50° C., and, after reaching this temperature, 3.10 g, (47.7 mmol) of zinc powder are added. This changes the color of the reaction solution from dark blue via turquoise to red-brown. The red-brown color is characteristic of the formation of an Ni(O) complex. This solution is stirred at 50° C. under argon as the inert gas for a total of 1 hour. 3.00 g (17.2 mmol) of 2-bromo-3-hydroxy-6-methylpyridine are then added to this solution in solid form. The dark red-brown reaction solution immediately clears to an orange-yellow color. The further course of the reaction is monitored by thin-layer chromatography (silica gel/petroleum ether (low-boiling):ether=75:25). The reaction is stopped after 2 hours by pouring the still warm reaction solution into 300 ml of 2N sodium hydroxide solution, during which triphenylphosphine is precipitated. The suspension obtained is vigorously stirred for 10 minutes and the product is then filtered off. This procedure is repeated once with the red-brown precipitate obtained (stirring for 10 minutes in 300 ml of 2N NaOH), giving 600 ml of a clear yellow solution. This solution is brought to a pH of 7-6 with concentrated hydrochloric acid, resulting in a light yellow, flocculent precipitate of the crude product. In order to obtain quantitative precipitation of the crude product, it is recommended to irradiate the solution with a UV lamp, ($\lambda_{max}$=365/366 nm). In this manner, quantitative precipitation can be detected accurately by the change in fluorescence from blue to light green. Care should be taken that the precipitated product has a green solid-state fluorescence. Immediately after precipitation, the precipitate obtained is filtered off, washed with water until neutral and dried in vacuo. The crude product obtained is recrystallized from 50 ml of toluene and finally concentrated to 25 ml for crystallization, giving brilliant green needles of the pure product.

Yield: 0.78 g (41.9%)—melting point 189°-190° C.—R$_F$ (silica gel/chloroform)=0.82—IR (KBr):$\nu$=3440 cm$^{-1}$ (m), 3100-2200 (m, OH) 1496 (s, aromatic), 1457 (w), 1447 (w), 1392 (m), 1369 (m), 1322 (m, OH), 1293 (s), 1239 (s), 1225 (m), 1133 (m, C—O), 1069 (m, C—O), 888 (s), 832 (s), 824 (s), 757 (w), 661 (m), 487 (w).—UV/VIS (chloroform): $\lambda_{max}$ ($\epsilon$)=353 nm (16671).—$^1$H-NMR (CDCl$_3$/TMS):$\delta$=2.20 (s, 6H, CH$_3$), 7.03 (d, J$_{5,4}$=J$_{5',4'}$=9 Hz, 2H, 5-H, 5'-H) , 7.27 (d, J$_{4,5}$=J$_{4',5'}$=9 Hz, 2H, 4-H, 4'-H). -MS (70 eV): m/z (%)=217 (13) M$^+$+1, 216 (100) M$^+$, 215 (6), 200 (11), 199 (79) M$^+$-OH, 188 (9), 187, (15), 159 (8), 135 (11), 118 (4), 108 (4), 92 (4), 91 (4), 79 (5), 80 (15), 53 (22), 40 (7).

C$_{12}$H$_{12}$N$_2$O$_2$ (216.2): Calculated C 66.65 H 5.59 N 12.95; Found C 66.59 H 5.61 N 12.65.

EXAMPLE 4

4,4'-Dihydroxy-3,3'-biisoquinoline a) Isoquinoline N-oxide

Isoquinoline N-oxide is synthesized by the procedure of M. M and B. L. Robison, J. Org. Chem. 21, (1956), 1337. Yield 60.0%—melting point 40°-100° C. (from ethyl acetate) as a mixed hydrate.

b) 4-Hydroxyisoquinoline (cf. E. Ochai, M. Tkebara, Pharm. Bull. 3 (1956), 454) 21.8 g (150 mmol) of isoquinoline N-oxide are dissolved in 400 ml of chloroform, thoroughly dried over magnesium sulfate and filtered. To this solution are added 31.2 g (164 mmol) of freshly recrystallized p-toluenesulfonic chloride, which dissolves with the evolution of heat. A solution of 20 g of sodium carbonate in 450 ml of water is added with vigorous stirring. This solution is stirred at room temperature for 15 hours. The organic phase is separated off, dried and the solvent is distilled off. 440 ml of 5M sulfuric acid are added to the red, oily residue obtained, and the entire mixture is heated to boiling for 24 hours. The cooled solution is neutralized with solid sodium carbonate, and the resulting light brown precipitate is filtered off.

Yield 10.6 g (48.4%)—melting point 207° C. (from acetone/acetic acid (6:1), dec.)

c) 3-Bromo-4-hydroxyisoquinoline 6.0 g (41 mmol) of 4-hydroxyisoquinoline are dissolved in 50 ml of 10% strength sodium hydroxide solution, giving a yellowish brown color. The reaction mixture is cooled to −5° C. using an ice/common salt mixture. A mixture comprising 6.6 g (2.1 ml, 41 mmol) of bromine dissolved in 50 ml of 10% strength sodium hydroxide solution is added dropwise to this solution over a period of 1 hour. During this period, the temperature of the reaction solution must never exceed 0° C. After this time, the coolant is removed and the reaction solution is stirred at room temperature for another 3 hours. The reaction solution is then cooled to −10° C. The reaction solution is then brought to a pH of 3 with 2N hydrochloric acid, during which the temperature of the reaction solution never exceeds −5° to 0° C. This gives the crude product as a light yellow solid. The crude product is recrystallized from 180 ml of ethyl acetate.

Yield 4.40 g (49.5%)—melting point 164° C.

d) 4,4'-Dihydroxy-3,3'-biisoquinoline 4.06 g (17.2 mmol) of $NiCl_2 \times 6H_2O$ are dissolved in 75 ml of technical grade DMF (green color). A continuous argon gas stream is passed through the reaction solution. After dissolution of all the $NiCl_2 \times 6H_2O$, 17.92 g (68.92 mmol) of triphenylphosphine are added. This leads to a dark blue color of the reaction solution due to the complexation with nickel. This solution is heated to 50° C., and, after reaching this temperature, 3.10 g (47.7 mmol) of zinc powder are added. This changes the color of the reaction solution from dark blue via turquoise to red-brown. The red-brown color is characteristic of the formation of an Ni(O) complex. This solution is stirred at 50° C. under argon as the inert gas for a total of 1 hour. 3.84 g (17.2 mmol) of 3-bromo-4-hydroxyisoquinoline are added to this solution in solid form. The further course of the reaction is monitored by thin-layer chromatrography [sic] (silica gel/petroleum ether (low-boiling):ether=9:1). The reaction is stopped after 2 hours by pouring the still warm reaction solution into 300 ml of 2N sodium hydroxide solution, during which triphenylphosphine is precipitated. The suspension obtained is vigorously stirred for 10 minutes and the product is then filtered off. This procedure is repeated once with the red-brown precipitate obtained (stirring for 10 minutes in 100 ml of 2N NaOH), giving 400 ml of a red-brown solution. This solution is brought to a pH of 7-6 with concentrated hydrochloric acid, resulting in a brownish precipitate of the crude product, which agglomerates to a large extent at a neutral pH. The aqueous neutral solution thus obtained is extracted with chloroform (4×50 ml) and dried directly over $Na_2SO_4$. It is concentrated on a rotary evaporator to give a dark red-brown crude product, which is recrystallized from 75 ml of toluene and finally concentrated to 50 ml for crystallization. Recrystallization leaves a light yellow, insoluble residue. Orange-brown crystals of the product, which are not yet analytically pure, crystallize from the mother liquor. They are taken up in 15 ml of chloroform and filtered through a silica gel acid [sic] (petroleum ether (low-boiling) diethyl ether=9:1). A dark brown insoluble residue remains on the column. At the same time, a light yellow solution is obtained which, after evaporation on a rotary evaporator, gives an orange powder. This powder is recrystallized again from 50 ml of toluene, giving brilliant orange needles of the pure product, which have a red solid-state fluorescence.

Yield: 0.68 g (27.4%)—melting point 270° C.—$R_F$ (silica gel/chloroform)=0.72.—IR (KBr): $\nu$=3060 $cm^{-1}$ (w), 2960-2470 (m, OH), 1592 (m), 1570 (m), 1489 (s), 1456 (m), 1398 (s, OH), 1336 (s, OH), 1315 (s, OH), 1224 (m), 1170 (m, C—O), 1156 (m, C—O), 1123 (m, C—O), 889 (m), 856 (w), 822 (m), 749 (s), 744 (s), 586 (m), 563 (m), 508 (m)—UV/VIS (chloroform): $\lambda_{max}$ ($\epsilon$)=388 nm (27677), 372 (24217).—$^1$H-NMR ($CDCl_3$/TMS):$\delta$=7.45-7.90 (m, 4H, 6-H, 6'-H, 7-H, 7'-H), 8.00 (dd, $J_{8,7}$=$H_{8',7'}$=8.0 Hz, $J_{8,6}$=$J_{8',6'}$=2.0 Hz, 2H, 8-H, 8'-H), 8.48 (dd, $J_{5,6}$=$J_{5',6'}$=8.0 Hz, $J_{5,7}$=$J_{5',7'}$=2.0 Hz, 2H, 5-H, 5'-H), 8.78 (s, 2H, 1-H, 1'-H). -MS (70 eV): m/z (%)=289 (57) $M^+$+1, 288 (100) $M^+$, 271 (71) $M^+$-OH, 231 (22), 204 (21), 171 (16), 144 (19), 116 (15), 89 (71), 63 (31), 39 (21).

$C_{18}H_{12}N_2O_2$ (288.3): Calculated C 74.99 H 4.19 N 9.71; Found C 75.20 H 4.32 N 9.79.

EXAMPLE 5

3,3-Dimethoxy-2,2'-biquinoline a) 3-Hydroxyquinoline 1.0 g (6.9 mmol) of 3-aminoquinoline are dissolved in 10 ml of 5N sulfuric acid (green-yellow color). The entire mixture is cooled to +5° C. in an ice bath. 0.5 g (7.2 mmol) of sodium nitrite is added to this solution. During this, care is taken that the temperature of the reaction solution never exceeds +5° C. During the addition, the reaction solution remains clear and turns slightly reddish. The reaction mixture thus obtained is stirred for another 10 minutes without ice cooling. The reaction mixture is then added dropwise over a period of 5 minutes to 30 ml of 2N sulfuric acid which has been heated to 70° C. During the dropwise addition, the yellowish reaction solution foams slightly. The reaction solution is stirred at this temperature for another hour. The reaction solution is then allowed to cool for 1.5 hours, resulting in the formation of crystals of a salt, which are filtered off with suction and dried in air. The mother liquor is brought to a pH of 8 with 5N sodium hydroxide solution, resulting in the isolation of more product. The salt obtained is dissolved in 2N sodium hydroxide solution and brought to a pH of 8 with 2N hydrochloric acid. In this manner, a beige precipitate of the free crude product is obtained. The combined charges of liquid product are recrystallized from 50 ml of ethanol.

Yield 0.92 g (92%)—melting point 192°-193° C.—$R_F$ (silica gel/ethanol)=0.75.—IR (KBr): $\nu$:3441 $cm^{-1}$, 3049 (m), 2957, 2675 (m, OH), 1612 (w), 1576 (s), 1345 (s), 1312 (m), 1291 (s), 1246 (s, C—O), 1185 (m, C—O), 1152 (s, C—O), 1091 (s, C—O), 974 (w), 906 (w), 789 (m), 725 (m), 623, 598 (m).—$^1$H-NMR (($D_6$)DMSO/TMS): $\delta$=7.40-7.57 (m, 2H, 6-H, 7-H), 7.70-8.87 (m, 2H, 5-H, 8-H), 8.75 (d, $J_{2,4}$=2.0 Hz, 1H, 2-H), 10.32 (s, 1H, OH).

b) 2-Bromo-3-hydroxyquinoline 6.0 mg (41 mmol) of 3-hydroxyquinoline are dissolved in 50 ml of 10% strength sodium hydroxide solution, giving a yellowish brown color. The reaction mixture is cooled to −5° C. using an ice/common salt mixture. A mixture comprising 6.6 g (2.1 ml, 41 mmol) of bromine dissolved in 50 ml of 10% strength sodium hydroxide solution is added dropwise to this solution over a period of 1 hour. During this the temperature of the reaction solution must never exceed 0° C. After this time, the cooling is removed and the reaction solution is stirred at room temperature for another 3 hours. The reaction solution is then cooled to −10° C. The reaction solution cooled to −10° C. [sic]. The reaction solution is then brought to a pH of 3 with 2N hydrochloric acid, during which the temperature of the reaction solution must never exceed −5° to 0° C. This gives the crude product as a light yellow solid. The crude product is recrystallized from 180 ml of ethyl acetate.

Yield 6.0 g (66.0%) (colorless platelets)—melting point 189°-190° C. (with conversion)—$R_F$ (silica gel/chloroform)=0.17.—IR Br): $\nu$=3500-3300 $cm^{-1}$ (m), 3190-2580 [illegible], OH), 1615 (m), 1550 (w), 1500 (s), 1430 (s), 1335 (s) 1275, 1235 (m, C—O), 1145 (m, C—O), 935, 910 (w), 815 (m), 750 (s), 640, 540, 422, 390 (w, C-Br)—$^1$H-NMR (($D_6$)DMSO/TMS): $\delta$=7.67 (mc, 2H, 6-H, 7-H), 8.00 (mc, 2H, 5-H, 8-H), 8.68 (s, 1H, 4-H), 11.17 (s, 1H, OH).

c) 2-Bromo-3-methoxyquinoline 6.30 g (113 mmol) of 80% pure potassium hydroxy [sic] powder are suspended in 40 ml of DMSO and heated to 50° C. under an argon stream. 5.0 g (22.5 mmol) of 2-bromo-3-hydroxyquinoline dissolved in 10 ml of DMSO are added to this suspension. After addition of the educt, the reaction temperature is maintained at this temperature for 10 minutes. The reaction solution has a dark yellow color. 10.4 g (4.5 ml, 28.1 mmol) of methyl iodide dissolved in 10 ml of DMSO are then added to this solution at such a rate that the temperature of the reaction solution remains between 50° and 55° C. The reaction solution is then stirred at this temperature for another 10 minutes. The finished red-brown reaction mixture is poured onto 120 ml of ground ice, resulting in the precipitation of the crude product as a gray solid. After recrystallization from 25 ml of petroleum ether, the product is obtained in the form of gray, fine needles.

Yield 0.75 g (70.0%)—melting point 85°–86° C.—$R_F$ (silica gel/chloroform) = 0.28.—IR (KBr): $\nu$ = 3500 cm$^{-1}$ (w, aromatic), 3060 (w, aromatic), 2980 (w, aliphatic), 2965 (w, aliphatic), 2855 (w, aliphatic), 1589 (s), 1556 (m), 1494 (s, aromatic), 1478 (m), 1449 (s), 1360 (m), 1354 (s), 1316 (s), 1285 (s), 1239 (s, C—O—C), 1183 (w), 1145 (s), 1067 (s), 1019 (m), 921 (w), 902 (m), 813 (m, aromatic), 744 (s), 639 (m), 425 (m, C-Br).—$^1$H-NMR (CDCl$_3$/TMS): $\delta$ = 4.14 (s, OCH$_3$), 7.49–7.61 (m, 2H, 6-H, 7-H), 7.96–8.12 (m, 2H, 5-H, 8-H), 8.66 (s, 1H, 4-H).

d) Direct coupling experiment of 2-bromo-3-hydroxyquinoline 1.59 g (6.70 mmol) of NiCl$_2$×6H$_2$O are dissolved in 75 ml of technical grade DMF (green color). A continuous argon gas stream is passed through the reaction solution. After dissolution of all the NiCl$_2$×6H$_2$O, 6.99 g (26.8 mmol) of triphenylphosphine are added. This leads to a dark blue color of the reaction solution due to the complexation with nickel. This solution is heated to 50° C., and, after reaching this temperature, 1.2 g (18.5 mmol) of zinc powder are added. This changes the color of the reaction solution from dark blue via turquoise to red-brown. The red-brown color is characteristic of the formation of an Ni(O) complex. This solution is stirred at 50° C. under argon as the inert gas for a total of 2.5 hours. 1.50 g (6.74 mmol) of 2-bromo-3-hydroxyquinoline are added to this solution in solid form. The further course of the reaction is monitored by thin-layer chromatography (silica gel/chloroform). The reaction is stopped after 2.5 hours by pouring the still warm reaction solution into 300 ml of 2N sodium hydroxide solution, during which triphenylphosphine is precipitated. The suspension obtained is vigorously stirred for 10 minutes and the product is then filtered off. This procedure is repeated once with the red-brown precipitate obtained (stirring for 10 minutes in 300 ml of 2N NaOH), giving 600 ml of a yellow solution (blue fluorescence). This solution is brought to a pH of 7–6 with concentrated hydrochloric acid. The precipitate is filtered off with suction and dried. The crude product obtained is dissolved in 20 ml of warm DMSO and separated by passing it through a column (silica gel/toluene: glacial acetic acid = 4:1). The coupling product is obtained as the first charge and has a weakly red fluorescence.

Yield 20 mg (2%)—melting point > 360° C.—$R_F$ (silica gel/toluene: glacial acetic acid = 4:1) = 0.63.

e) 3,3'-Dimethoxy-2,2'-biquinoline 0.99 g (4.20 mmol) of NiCl$_2$×6H$_2$O is dissolved in 100 ml of technical grade DMF (green color). A continuous argon gas stream is passed through the reaction solution. After dissolution of all the NiCl$_2$×6H$_2$O, 4.41 g (16.8 mmol) of triphenylphosphine are added. This turns the reaction solution dark blue due to the complexation with nickel. This solution is heated to 50° C. and, after reaching this temperature, 2.00 g (30.8 mmol) of zinc powder are added. This changes the color of the reaction solution from dark blue via turquoise to red brown. The red-brown color is characteristic of the formation of an Ni(O) complex. This solution is stirred at 50° C. under argon inert gas for a total of 3 hours. 1.0 g (4.2 mmol) of 2-bromo-3-methoxyquinoline is then added to this solution in solid form. The further course of the reaction is monitored by thin-layer chromatography (silica gel/chloroform). The reaction is stopped after 8 hours by pouring the still warm reaction solution into 200 ml of 2N hydrochloric acid, giving a dirty brown precipitate which after some time forms oily lumps. The suspension obtained is filtered, giving a yellow solution. The aqueous phase is still slightly cloudy and is therefore filtered once more. The solution is then brought to a pH of 12 with 10% strength sodium hydroxide solution, resulting in a colorless, voluminous precipitate. This precipitate is filtered off with suction and washed with water until neutral. The crude product is boiled in 60 ml of toluene, giving a green inorganic residue. The organic phase has a yellow color and shows a greenish fluorescence. The toluene is evaporated off, and the yellowish solid obtained is suspended once more in 10 m [sic] of concentrated hydrochloric acid. The yellow solution is filtered, giving the remaining triphenylphosphine as residue. The solution is brought to a pH of 12 with 10% strength sodium hydroxide solution, and the colorless pure product is washed until neutral. After drying, the product is recrystallized from 30 ml of toluene, giving colorless crystals.

Yield 0.20 g (30.3%)—melting point: 258° C.—$R_F$ (silica gel/touene [sic]:glacial acetic acid = 80:20) = 0.49.—IR (KBr): $\nu$ = 3429 cm$^{-1}$ (m), 3060 (w), 3035 (w), 3012 (w), 2968 (w), 2945 (w), 2840 (w), 1574 (s), 1565 (m), 1508 (m), 1497 (s), 1474 (s), 1303 (s), 1279 (s), 1237 (m), 1234 (m), 1141 (m), 1070 (m), 1052 (m), 1017 (m), 971 (m), 786 (m), 771 (s), 595 (w).—UV (chloroform): $\lambda_{max}$ ($\epsilon$) = 338 nm (10023), 326 (9647), 299 (7674).—$^1$H-NMR —((D$_6$)DMDO/TMS): $\delta$ = 0.87 (s, 6H, OCH$_3$), 6.93–7.75 (m,. 6H, 5-H, 5'-H, 6-H, 6'-H, 7-H, 7'-H), 8.08 (dd. J$_{8,7}$ = J$_{8',7'}$ = 8.0 Hz, J$_{8,6}$ = J$_{8',6'}$ = 2.0 Hz, 2H, 8-H, 8'-H), 9.03 (s, 2H, 4-H, 4'-H). -MS (70 eV):m/z (%) = 317 (22) M+1, 316 (100) M+, 301 (9) M+-CH$_3$, 286 (6), 285 (6), 273 (13), 258 (13), 242 (12), 229 (13), 216 (15), 203 (15), 189 (5), 176 (8), 44 (6), 43 (6).

C$_{20}$H$_{16}$N$_2$O$_2$ (316.3): Calculated C 75.93 H 5.10 N 8.85; Found C 75.82 H 5.28 N 8.68.

EXAMPLE 6

3-Hydroxy-3'-methoxy-2,2'-biquinoline 240 mg (0.75 mmol) of 3,3'-dimethoxy-2,2'-biquinoline are suspended in 15 ml of 30 percent strength HBr in glacial acetic acid. In the course of heating, the educt soon dissolves. After as little as about 1 hour, the first crystals of the hydrobromide precipitate. The reaction solution is constantly refluxed. After 8 hours, another 5 ml of 30 percent strength HBr in glacial acetic acid are added. The reaction is stopped after 24 hours. The reaction mixture is diluted to 100 ml with water. This dissolves the precipitate formed. The aqueous phase is brought to a pH of 11 with solid sodium hydroxy [sic] pellets and extracted with 50 ml of chloroform. The aqueous phase is then brought to a pH of 6 with concentrated hydrochloric acid and extracted with 250 ml of chloroform (5×50 ml). The chloroform phase is dried over CaCl$_2$ and evaporated on a rotary evaporator (beige crude product). The crude product is purified on a column (silica gel/chloroform). Finally, the product is recrystallized from 10 ml of toluene, giving colorless crystals of pure substance. Yield 0.19 g (86.4%)—melting point 255° C. dec.—R$_F$ (silica gel/toluene:glacial acetic acid=4:1)=0.26.—IR (KBr):$\nu$=3422 cm$^{-1}$ (m), 3066 (m), 2938 (m), 2842 (m), 3010-2280 (m, OH), 1576 (m), 1501 (m), 1465 (m), 1424 (w), 1375 (w), 1332 (m), 1309 (s), 1279 (s), 1241 (m), 1214 (w, C—O), 1200 (w), 1161 (w, C—O), 1143 (s), 1061 (w), 995 (w), 758 (s).—UV (chloroform): $\lambda_{max}$ ($\epsilon$)=335 nm (8326), 327 (8062), 298 (6134).—$^1$H-NMR ((D$_6$) DMSO/TMS): $\delta$=3.90 (s, 3H, OCH$_3$), 7.00-7.70 (m, 6H, 5-H, 5'-H, 6-H, 6'-H, 7-H, 7'-H), 8.18 (d. J$_{8,7}$=J$_{8',7'}$=8.0 Hz, 2H, 8-H, 8'-H), 8.90 (s, 1H, 4'-H) 9.03 (s, 1H, 4-H).—MS (70 eV): m/z (%)=303 (18) M$^+$+1, 302 (100) M$^+$, 301 (9), 288 (8), 287 (46) M$^+$CH$_3$, 286 (6), 271 (4), 259 (11), 258 (5), 242 (5), 241 (5), 231 (13), 230 (5), 229 (4), 204 (7), 203 (10), 177 (4), 176 (10), 88 (5), 57 (5), 43 (5), 41 (6).

C$_{19}$H$_{14}$N$_2$O$_2$: (302.1) Calculated C 75.53 H 4.67 N 9.27; Found C 75.24 H 4.69 N 9.52.

EXAMPLE 7

3,3'-Dihydroxy-2,2'-biquinoline 200 mg (0.63 mmol) of 3,3'-dimethoxy-2,2-biquonoline [sic] are heated to 130° C. in 10 ml of hydroiodic acid, resulting in the formation of a rust-brown precipitate. The reaction is stopped after 3 hours, and the reaction solution is poured into 60 ml of water. This does not dissolve the precipitate obtained, and the solution is orange-colored. It is made neutral using 2N sodium hydroxide, which initially dissolves the orange precipitate and gives a yellow precipitate. The crude product obtained is recrystallized from isopropanol (40 ml) by extraction, giving the pure substance as a colorless powder.

Yield 0.17 g 94.4%)—melting point>360° C.—R$_F$ (silica gel/i-propanol)=0.82.—IR (KBr): 3420 cm$^{-1}$ (m), 3067-2550 (m, OH), 1574 (m), 1508 (m), 1503 (m), 1466 (m), 1425 (w), 1400 (w), 1376 (m), 1332 (s), 1281 (w), 1249 (w), 1217 (s), 1161 (w), 1141 (s), 755 (s).—UV/VIS (chloroform): $\lambda_{max}$ ($\epsilon$)=399 nm (9202), 328 nm (7975).—$^1$H-NMR ((D$_6$)DMSO/TMS): $\delta$:6.96-7.58 (m, 6H, 5'-H, 5'-H, 6-H, 6'-H, 7-H, 7'-H), 7.98 (d, J$_{8,7}$=J$_{8',7'}$8.0 Hz, 2H, 8-H, 8'-H), 8.87 (s, 2H, 4-H, 4'-H).—MS (70 eV): m/z (%)=298 (18) M$^+$+1, 288 (100) M$^+$, 287 (16), 271 (7) M$^+$-OH, 260 (7), 259 (17), 232 (5), 231 (9), 204 (7), 176 (s), 88 (4).

C$_{18}$H$_{12}$N$_2$O$_2$: (288.3), Calculated C 74.99 H 4.19 N 9.72; Found C 74.73 H 4.34 N 0.79.

EXAMPLE 8

Synthesis of 3,3'-dimethoxy-2,2'-biquinoline via organotin compounds a) Quinoline hydrochloride 50.0 g (30.7 ml, 387 mmol) of quinoline are dissolved in 100 ml of cyclohexane. Hydrogen chloride prepared from 116 g (2.00 mol) of NaCl and 196 g (106 ml, 2.00 mol, d=1.841) of sulfuric acid is introduced into the solution. This precipitates the hydrochloride as a colorless solid in flocculent form. The product is filtered off with suction several times, and more hydrogen chloride gas is introduced into the mother liquor. The colorless product obtained is recrystallized from ethanol, converting the product into colorless platelets.

Yield 18.7 g (the yield can be increased by introducing further hydrogen chloride gas)—melting point 70° C.

b) 3-Bromoquinoline 18.0 g (112 mmol) of quinoline hydrochloride are taken up in 22 ml of nitrobenzene. The reaction solution is heated to 180° C., as a result of which the educt goes into solution. 6.20 ml (123 mmol) of bromine are added dropwise to this solution over a period of 30 minutes. The reaction solution is kept at this temperature for 4.5 hours. After a reaction time of as little as 1 hour, the hydrobromide starts precipitating in the reaction solution as an orange-brown precipitate. Finally, the reaction is cooled to 80° C., and 90 ml of benzene are added to the reaction solution. This precipitates the hydrobromide (yield 25.3 g). The hydrobromide is poured into 150 ml of water, and the solution is brought to a pH of 7-8 with Na$_2$CO$_3$. This converts the hydrobromide into a brown oil. The crude product is extracted from the aqueous phase using a total of 500 ml of ether, and the ether phase is washed twice with 50 ml each time of water. After evaporation of the ether, the crude product is obtained as a dark-brown oil. The crude product is distilled at 10$^{-3}$ mm Hg, converting the product into a light yellow oil.

Yield 44.3 g (60.8%—boiling point 73.0° C. (10$^{-3}$ mm Hg (0.5 mm Hg).—IR (KBr): $\nu$=3062 cm$^{-1}$ (m), 1583 (s), 1494 (s), 1413 (w), 1355 (m), 1317 (s) 1193 (m), 1127 (m), 1073 (s), 943, 895 (s), 859 (w), 848, 781 (s), 765 (w), 749 (s), 625, 583, 473, 409 (m, C-Br).

c) 2-Trimethylstannyl-3-methoxyquinoline 3.00 g (131 mmol) of sodium are introduced in a sealed Schlenck-type apparatus under argon inert gas into 3 ml of DME$_{abs.}$ (=absolute dimethoxyethane). The sodium is cut into very small pieces and, before being added to the reaction solution washed with DME$_{abs}$ to remove any adhering paraffin. During addition of the sodium to the reaction solution, the DME$_{abs.}$ slightly foams. The reaction solution is then cooled to $-10$° C. using an ice/common salt mixture. 0.83 g (4.18 mmol) of trimethyltin chloride is added to this solution. After a reaction time of 2 hours, the reaction solution is colorless, milky and cloudy. After a total of 3 hours, the reaction solution has become milky, cloudy and green. This can be considered as an indication of the formation of sodium trimethylstannate. Excess sodium is removed from the reaction solution under argon via a D-2 Schlenck-type frit. 0.35 g (1.45 mmol) of 2-bromo-3-methoxyquinoline (20) dissolved in 3 ml of DME$_{abs.}$ is added dropwise to the filtered cloudy green reaction solution. Upon dropwise addition of the educt, the reaction solution spontaneously turns blood red. After a short time, the reaction solution has a brown color. After 30 minutes, the reaction solution finally turns beige. The solution is stirred at $-10$° C. for a total of 3 hours, during which the color of the reaction solution no longer changes. After the reaction is complete, the product mixture is filtered through a D-4 frit to remove the precipitate. The precipitate is washed with DME$_{abs.}$ without vacuum, the runoff being dark brown. A colorless solid remains in the frit. Upon evaporation of the filtrate in a rotary evaporator, a dark-brown oil is obtained whose composition is analyzed by $^1$H-NMR spectroscopy. Explicit purification of the product is omitted due to the sensitivity to hydrolysis. The product content is determined by spectroscopy. The hydrolysis product 3-methoxyquinoline can be detected as a by-product of this reaction. This finding is confirmed by the $^1$H-NMR experiments described below.

Yield 82.9% (determined by $^1$H-NMR spectroscopy) and 17.0% of 3-methoxyquinoline—$R_F$ (silica gel/chloroform)=0.16.—$^1$H-NMR (CDCl$_3$/TMS): δ=0.47 (s, 9H, Sn(CH$_3$)3), 3.90 (s, 3H, OCH$_3$), 7.27 (mc, 2H, 6-H, 7-H), 7.73 (mc, 1H, 5-H), 7.97 (mc, 1H, 8-H), 8.57 (s, 1H, 4-H).

Below, various additional signals in the $^1$H-NMR of the reaction product are identified by adding authentic samples. The substances are identified by using the methoxy signals of the individual substances in each case:

1. Addition of the hydrolysis product 3-methoxyquinoline:

The methoxy signal at 3.67 ppm increases in intensity. 3-Methoxyquinoline can be detected as the only by-product (17%) of the reaction by means of the methoxy signal.

2. Addition of the educt 2-bromo-3-methoxyquinoline:

Upon addition of the educt, a completely new methoxy signal appears at 4.07 ppm. From this, it can be concluded that the reaction goes to completion.

3. Addition of trimethyltin chloride:

A new signal appears at 0.33 ppm. This is due to the methyl groups in the educt. In this manner, it can be ruled out that the strong high-field signal at 0.47 ppm is due to contamination by trimethyltin chloride.

d) 2-Trimethylstannyl-3-methoxyquinoline 3.00 g (130 mmol) of sodium are introduced in a sealed Schlenck-type apparatus under argon inert gas into 3 ml of absolute DME. The sodium is cut into very small pieces and, before being added to the reaction solution, is washed with absolute DME to remove any adhering paraffin. After the sodium has been suspended in DME, the reaction solution remains clear, and only a slight evolution of gas can be observed. The reaction mixture is cooled to −10° C. using an ice/common salt mixture and 1.16 g (5.84 mmol) of trimethyltin chloride are then added in solid form. After the addition, the reaction solution still remains clear. After a reaction time of 1 h, the reaction solution has a milky cloudy color. After a reaction time of 3 hours, the reaction solution becomes milky, gray and cloudy. Shortly afterwards, the reaction solution turns deep green. The solution is stirred for a total of 4 hours. The last hour of the reaction is carried out without ice cooling. In order to remove excess sodium, the reaction solution is filtered under argon inert gas through a D-2 Schlenck-type frit. 0.70 g (2.92 mmol) of 2-bromo-3-methoxyquinoline dissolved in 3 ml of absolute DME is added dropwise to the filtered cloudy and green reaction solution. Upon dropwise addition of the educt, the reaction solution spontaneously turns blood red. During the addition of the educt, the reaction solution is cooled with ice. After a short time, the reaction solution has a dark brown color, which, after a reaction time of 1.5 hours, clears to light brown. After a reaction time of 4 hours with ice cooling, the reaction mixture is filtered through a D-4 frit to remove the solids formed. This gives a light yellow reaction solution. A gray solid remains in the frit. The solvent is washed with more [lacuna], the runoff being dark brown. After evaporation of the solvent, a dark brown oil is obtained. A thin-layer chromatogram obtained in chloroform shows that the desired product is obtained. Slight traces of the hydrolysis product 3-methoxyquinoline can be detected by $^1$H-NMR spectroscopy.

Yield 0.79 g (mixture of product and by-product)—$R_F$ (silica gel/chloroform)=0.16; =0.86 (by-product).—$^1$H-NMR (CDCl$_3$/TMS): δ=0.47 (s, 9H, Sn(CH$_3$)3), 3.90 (s, 3H, OCH$_3$), 7.27 (mc, 2H, 6-H, 7-H), 7.73 (mc, 1H, 5-H), 7.97 (mc, 1H, 8-H), 8.57 (s, 1H, 4-H).

e) 3,3'-Dimethoxy-2,2'-biquinoline

Toluene is distilled over LiAlH$_4$ and made absolute in this manner directly before reaction. Under argon inert gas, 0.79 (2.46 mmol) of the 2-trimethylstannyl-3-methoxyquinoline described above is taken up in 5 ml of absolute toluene. 0.61 g (2.51 mmol) of 2-bromo-3-methoxyquinoline is then added to this solution. The reaction solution has a yellow color. To [sic] 20 mg (0.017 mmol) of tetrakis(triphenylphosphine) palladium(O) are then added to the reaction solution, and the reaction is monitored by thin-layer chromatography (silica gel/Et$_2$O). The reaction solution is heated to boiling. After a reaction time of 20 hours, the tin compound and the bromine compound can still be detected. At the same time, a new band having an $R_F$ value of 0.25 and yellow fluorescence, which can be assigned to the desired product, can be detected. After a reaction time of 50 hours, another 0.010 g (0.008 mmol) of catalyst is added. After a total reaction time of 75 hours, the reaction is finally stopped. The educt can no longer be detected in the thin-layer chromatogram. The dark brown reaction solution obtained is filtered. A brownish precipitate remains and a reddish brown solution is obtained. This solution is evaporated on a rotary evaporator and taken up in diethyl ether. The reaction mixture is separated on a silica gel column using diethyl ether as the eluent. Five charges are obtained, of which the first is triphenylphosphine, the second a decomposition product of the organotin compound having a blue fluorescence, the third is 2-bromo-3-methoxyquinoline, the fourth is a small amount of a non-identified by-product and the fifth is 3,3'-dimethoxy-2,2'-biquinoline.

Yield 10 mg (2.5%) (light yellow powder)—melting point 215°–218° C. (after chromatography)—$R_F$ (silica gel/diethyl ether)=0.25.—$^1$H-NMR (CDCl$_3$/TMS): δ=3.83 (s, OCH$_3$), 6.93–7.66 (m, 6H, 5, 5'-H, 6, 6'-H, 7,7'-H), 8.15 (d, $J_{7,8}=J_{7'8'}=8.0$ HZ[sic], 2H, 8,8'-H), 8.90 (s, 2H, 4,4'-H).—MS (0 eV): m/z (%) 316 (0.5, M+), 291 (0.5), 284 (0.8), 278 (3.0), 277 (4.9), 240 (3.1), 239 (18.5), 238 (3.1), 237 (19.8), 196 (11.1), 195 (8.6), 194 (12.3), 193 (22.2), 173 (44.4), 130 (24.7), 44 (23.5), 38 (34.6), 36 (100.0).

f) 3,3'-Dimethoxy-2,2'-biquinoline - shortened reaction time

The organotin compound is prepared completely analogously to the previous reaction. 0.25 g (1.04 mmol) of 2-bromo-3-methoxyquinoline, 0.41 g (2.08 mmol) of trimethyltin chloride and 1.50 g (65.4 mmol) of sodium are reacted in 7 ml of DME$_{abs}$. After usual workup, a mixture of 0.13 g (0.40 mmol) of 2-trimethylstannyl-3-methoxyquinoline is obtained according to $^1$H-NMR spectroscopy, which corresponds to a yield of 30%. Furthermore, 0.16 g (0.70 mmol) of unconverted 2-bromo-3-methoxyquinoline, which corresponds to a yield on [sic] 70%, is detected in this manner as unconverted educt. The product mixture is dissolved in 5 ml of absolute xylene (mixture of isomers) (yellow color).

20 mg (0.017 mmol) of tetrakis(triphenylphosphine)-palladium(O) are added to this solution. The reaction solution is refluxed under argon inert gas for 16 hours. After this time, the reaction solution has a dark brown color. After filtration, the reaction mixture is placed on a silica gel column using diethyl ether as the eluent, and separated as described above. This gives a light yellow powder. The spectroscopic data are identical to those of the previous reaction.

Yield 0.02 g (5.00%)—melting point: 244°–245° C. (after chromatography).

We claim:

1. A process for marking of articles comprising
   a) employing a bipyridyl as an ink wherein said bipyridyl is of the general formula

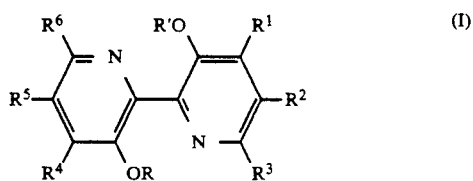

(I)

in which

R,R', independently of one another, are hydrogen, alkyl or alkylcarbonyl, $R^1$, $R^2$, $R^3$, $R^4$, $R^5$, $R^6$, independently of one another, are hydrogen, or alkyl and also $R^1$ and $R^2$ or $R^2$ and $R^3$, and/or $R^4$ and $R^5$ or $R^5$ and $R^6$ together with the pyridine ring to which they are bound can be a fused-on phenyl ring, which can also be substituted, under the condition that $R^1$, R2, $R^4$, $R^5$ are not hydrogen if $R^3$ and $R^6$ are hydrogen or methyl; and b) marking said article with said bipyridyl ink.

2. The process as claimed in claim 1, wherein said bipyridal ink is a signaling ink, for marking of signs in which it is desired to obtain a particular optical color impression.

3. The process as claimed in claim 1, wherein said bipyridal ink is used for safety markings, in which it is desired to obtain a particular unmistakable color.

4. The process as claimed in claim 1, wherein said ink is fluorescent.

5. A process for sorting the marked articles as claimed in claim 1, comprising sorting said marked articles by machine detection of said ink.

6. The process as claimed in claim 1 wherein said bipyridal is 4,4'-bishydroxy-3,3'-biisoquinoline of the formula II

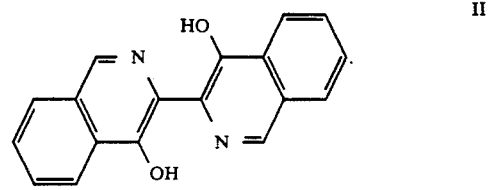

II

7. The process as claimed in claim 2 wherein said signaling inks are for the optical high-lighting of characters of drawings.

8. The process as claimed in claim 3, wherein the safety markings are applied on checks, check cards, bills, coupons, or identification papers.

* * * * *

UNITED STATES PATENT AND TRADEMARK OFFICE
CERTIFICATE OF CORRECTION

PATENT NO. : 5,266,700
DATED : November 30, 1993
INVENTOR(S) : Langhals, et. al.

It is certified that error appears in the above-indentified patent and that said Letters Patent is hereby corrected as shown below:

In the specification at column 6, lines 25-34, the formula (III) should read:

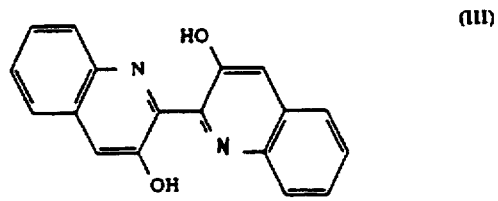

(III)

In the specification at column 21, lines 31 and 32, the word "biquonoline[sic]" should read --biquinoline--.

Signed and Sealed this

Eleventh Day of October, 1994

Attest:

BRUCE LEHMAN

*Attesting Officer*   Commissioner of Patents and Trademarks